(12) United States Patent
Sembo et al.

(10) Patent No.: US 7,601,362 B2
(45) Date of Patent: Oct. 13, 2009

(54) GELLED BAIT

(75) Inventors: Satoshi Sembo, Nishinomiya (JP); Kenya Okada, Takarazuka (JP)

(73) Assignee: Sumitomo Chemical Company, Limited, Osaka (JP)

(*) Notice: Subject to any disclaimer, the term of this patent is extended or adjusted under 35 U.S.C. 154(b) by 980 days.

(21) Appl. No.: 10/865,934

(22) Filed: Jun. 14, 2004

(65) Prior Publication Data

US 2004/0253288 A1 Dec. 16, 2004

(30) Foreign Application Priority Data

Jun. 16, 2003 (JP) ............... 2003-170384

(51) Int. Cl.
*A01N 25/04* (2006.01)
*A01N 43/08* (2006.01)
(52) U.S. Cl. .............. 424/405; 424/407; 514/471
(58) Field of Classification Search .............. 424/405; 514/471
See application file for complete search history.

(56) References Cited

U.S. PATENT DOCUMENTS 6,218,416 B1 * 4/2001 Sembo ............... 514/389
6,566,378 B1 * 5/2003 Saito ............... 514/344

FOREIGN PATENT DOCUMENTS

| GB | 2 336 111 A | 10/1999 |
| JP | 2000-053505 A | 2/2000 |
| WO | WO 91/07972 A1 | 6/1991 |
| WO | WO 00/04776 A1 | 2/2000 |

* cited by examiner

*Primary Examiner*—Neil Levy
(74) *Attorney, Agent, or Firm*—Sughrue Mion, PLLC

(57) ABSTRACT

An effective gelled poison bait is provided for the control of such objective insect as cockroaches, wherein the bait comprises 1-methyl-2-nitro-3-[(tetrahydrofuryl)methyl]guanidine, carrageenan, polyvinyl alcohol, at least one selected from fats and fatty oils and water.

3 Claims, No Drawings

GELLED BAIT

TECHNICAL FIELD

The present invention is generally directed to a gelled poison bait.

BACKGROUND ART

Poison baits are well known as being useful in controlling insects such as cockroaches, ants and the like. Such poison baits typically contain an edible composition that provides control over the insect after said insect has ingested the poison bait. Since the poison baits also generally contain a insecticidal compound, there is typically a greater insect controlling activity associated with said baits when large quantities of insects ingest said baits, and conversely a smaller insect controlling activity when a smaller quantity of insects ingest said baits.

Gelled poison baits are proposed since they are suitable for applying on vertical plane. GB-2336111 and WO 91-07972 describe poison baits which comprise carrageenan as an insect attractant as well as a gelling agent. Carrageenan is effective attractant; however, a poison bait that is practically useful should comprise a fat and/or fatty oil.

On the other hand, JP 2000-53505A discloses an aqueous bait comprising 1-methyl-2-nitro-3-[(tetrahydrofuryl)methyl]guanidine, which is an insecticidal ingredient and described in EP-649845A. The insecticidal ingredient, 1-methyl-2-nitro-3-[(tetrahydrofuryl)methyl]guanidine, is water-soluble and easily formulated to an aqueous solution for bait. However, it was difficult to obtain a gelled bait comprising a fat and/or fatty oil that is effective for controlling harmful insects constantly for a long time. It may come from the hydrophilicity of the insecticidal ingredient in fat or fatty oil.

SUMMARY OF THE INVENTION

The present invention provides a stable gelled poison bait that can serve to effectively control of insects, including cockroaches, ants and the like. The gelled poison bait of the present invention comprises (1) 1-methyl-2-nitro-3-[(tetrahydrofuryl) methyl]guanidine as an insecticidally active ingredient, (2) carrageenan, (3) polyvinyl alcohol, (4) at least one selected from fats and fatty oils and (5) water.

DETAILED DESCRIPTION OF THE INVENTION

In the present invention, the insecticidally active ingredient is 1-methyl-2-nitro-3-[(tetrahydrofuryl)methyl]guanidine of the formula:

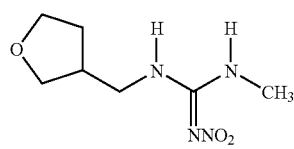

(I)

which is named dinotefuran as a common name.

Dinotefuran is disclosed in EP-649845A and can be prepared according to the description. The content of the dinotefuran in the gelled poison bait of the present invention is generally 0.01 to 2% by weight.

Carrageenan is a sulfated polysaccharide, derived from red algae. Several forms of carrageenan are known and kappa (κ)-carrageenan is preferably used in the present invention. The content of the carrageenan in the gelled poison bait of the present invention is generally 1 to 10% by weight.

Polyvinyl alcohol is produced by hydrolysis of polyvinyl acetate in the presence of acid or alkali. The content of the polyvinyl alcohol in the gelled poison bait of the present invention is generally 0.1 to 3% by weight. Further, the weight ratio of the polyvinyl alcohol to the carrageenan is generally in the range of between 1:4 and 1:8.

Fats and fatty oils are made up predominantly of trimesters of glycerin with fatty acids, and commonly are called triglycerides. Customarily fats, also known as lipids, are solids at ambient temperatures and oils are liquids. Examples of the fat include butter, margarine, peanut butter, palm butter, lard and beef tallow. Examples of the fatty oil include vegetable oils such as sesame oil, soybean oil, rapeseed oil, wheat germ oil, cottonseed oil, corn oil, sunflower oil, coconut oil and palm kernel oil; and animal oils such as whale oil, sardine oil and cod-liver oil. The content of the fat and/or fatty oil in the gelled poison bait of the present invention is generally 0.85 to 28.5% by weight. Further, the amount of the fat and/or fatty oil is generally 8.5 to 9.5 parts by weight per one part by weight of the polyvinyl alcohol.

Water is used for gelation. The content of the water in the gelled poison bait is an amount sufficient for forming gel, and it is usually 0.1 to 10% by weight.

If so desired, the gelled poison bait of the present invention may further comprise at least one selected from powdered crops, starch, dextrin and sugars. The content in the gelled poison bait of the present invention is generally 3 to 80% by weight. Examples of the powdered crops include flour, cereals, powders of corn, potato, sweat potato and rice. The starch may be made from maize, potato, sweat potato, wheat or rice. Dextrin, which is a glucose polymer in the hydrolysis of starch, when incorporated in the gelled poison bait of the present invention, may be obtained from the hydrolysis of starches, which have traditionally been obtained from maize, potato, sweat potato, wheat, rice or the like by the use of acids, heat or amylases. Sugars, which are carbohydrate compounds that may be utilized in the present invention, are usually soluble in water, and are exemplified by sucrose, glucose, fructose, lactose, raw sugar, brown sugar, molasseses, mixtures thereof and the like.

Further, the gelled poison bait of the present invention may optionally comprise sauce or sauce flavor. They are exemplified by Worcestershire sauce, cooking sauce and sauce flavors (e.g. Sauce flavor No. B-82404 and Saucemicron No. 600, which are produced by Takasago International Corporation). The content in the gelled poison bait of the present invention is generally 1 to 5% by weight.

Furthermore, the gelled poison bait of the present invention may optionally comprise glycerin. The content of the glycerin in the gelled poison bait of the present invention is generally 1 to 10% by weight.

The gelled poison bait of the present invention may comprise preservative or the other insecticidal compound than dinotefuran. Examples of the preservative include potassium sorbate, p-hydroxybenzoate (e.g. methyl p-hydroxybenzoate, ethyl p-hydroxybenzoate, butyl p-hydroxybenzoate) and salicylic acid derivatives. The content of the preservative in the gelled poison bait of the present invention is generally 0.1 to 5% by weight. Examples of the insecticidal compound include organophosphorus compounds, carbamate compounds, chitin synthesis inhibiting compounds, juvenile hormone compounds, arylazole compounds, hydramethylnon and boric acid.

The gelled poison bait of the present invention can be prepared, for example, by mixing dinotefuran, carrageenan, aqueous polyvinyl alcohol solution, fat and/or fatty oil and optionally powdered crop, starch, dextrin, sugar, sauce, sauce flavor, glycerin, preservative, the other insecticidal compound and so on under heating, and cooling the resulted mixture to room temperature or approximately 25° C.

The gelled poison bait of the present invention can be employed in various methods to control objective insects, and an example of such an insect controlling method includes setting, placing or applying an effective amount of one of the gelled poison bait in a location that the objective insects inhabit or are otherwise present. It is more convenient to use an applicator gun or syringe, for example, BaitGun (trademark of EFD Inc.) when the gelled poison bait is applied. The applicator gun or syringe is available on the market, and its use makes it easy to apply the gelled poison bait on a vertical plane or to a crevice where insects pass.

The amount of the application is generally 0.01 to 20 g, preferably 0.1 to 5 g of dinotefuran per 1 m$^2$ of the area where the gelled poison bait is being utilized to control objective insects.

The gelled poison bait of the present invention is well suited for controlling cockroaches (*Dictyoptera*) such as American cockroach (*Periplaneta americana*), German cockroach (*Blattella germanica*) and smokybrown cockroach (*Periplaneta fuliginosa*), and it is further suited for controlling ants (*Formicidae*) such as little ant (*Monomorium nipponensis*) and *Formica japonica*, death watch beetles (*Anabiidae*) such as tobacco beetle (*Lasioderma serricorne*) and biscuit beetle (*Stegobium paniceum*), Tenebrionid beetles (*Tenebrionidae*) such as red flour beetle (*Tribolium castaneum*) and confused flour beetle (*Tribolium confusum*), flat bark beetles (*Cucujidae*) such as the sawtoothed grain beetle (*Oryzaephilus surinamensis*) and flat grain beetle (*Cryptolestes pusillus*), termites (*Isoptera*) such as the Formosan subterranean termite (*Coptotermes formosanus*) and *Reticulitermes speratus*.

EXAMPLE

The present invention is explained in more detail by following examples.

Example 1

Five grams (5.0 g) of peanut butter (produced by Aohata Corporation), 9.0 g of sesame oil (produced by Kadoya Sesame Mills Inc.) and 5.0 g of glycerin were mixed under heating. To the mixture, 5.0 g of an aqueous polyvinyl alcohol solution (20% by weight, Gohsenol GL-05 produced by The Nippon Synthetic Chemical Industry Co., Ltd.), 2.0 g of Worcestershire sauce (produced by Kagome Co., Ltd.) and 31 g of molasseses (produced by Nakanihonhyoto Co., Ltd.) were added under heating and stirred to be uniform. Further, 0.5 g of dinotefuran, 2 g of potassium sorbate, 34.5 g of dextrin and 6 g of κ-carrageenan were added in sequence and stirred, and then the mixture was cooled to room temperature to afford 100 g of a gelled poison bait of the present invention.

Examples 2-4

The same procedures as Example 1 except that the amounts of the raw materials were changed according to the following table afforded the gelled poison baits of the present invention.

TABLE 1

|  | Example 1 | Example 2 | Example 3 | Example 4 |
| --- | --- | --- | --- | --- |
| dinotefuran | 0.5 g | 0.5 g | 0.5 g | 0.5 g |
| 20% polyvinyl alcohol solution | 5 g | 5 g | 5 g | 5 g |
| κ-carrageenan | 6 g | 6 g | 6 g | 6 g |
| dextrin | 34.5 g | 32 g | 37 g | 39.5 g |
| molasses | 31 g | 33 g | 29 g | 27 g |
| sesame oil | 9 g | 9.5 g | 8.5 g | 8 g |
| peanut butter | 5 g | 5 g | 5 g | 5 g |
| glycerin | 5 g | 5 g | 5 g | 5 g |
| Worcestershire sauce | 2 g | 2 g | 2 g | 2 g |
| potassium sorbate | 2 g | 2 g | 2 g | 2 g |
| Total | 100 g | 100 g | 100 g | 100 g |

Example 5

The gelled poison bait obtained by Example 1 was charged into a syringe. The syringe was attached to an application gun (Application Gun for CB Kit produced by Waterbury Companies, Inc.) and the gelled poison bait was extruded on an aluminum sheet by the application gun. The gelled poison bait on the aluminum sheet was hold vertically and there was no dripping for one hour.

The test result shows that the gelled poison bait of the present invention is useful for applying on a vertical plane without dripping.

Example 6

Solid feeding materials for animals (CE-2, produced by Oriental Yeast Co., Ltd.), a vessel containing water therein, a hiding shelter wherein 3 pieces of veneer were assembled into a triangular tube shape that has a 15 cm length and 3.5 cm width, and 10 of each male and female German cockroaches were inserted into a 27.8 cm×39.8 cm×height 7.5 cm plastic container and left overnight so that the cockroaches could acclimatize to said shelter. Subsequently, 1 g of the gelled poison bait obtained in Example 1 was spread on one outer surface and 1 g of a gelled bait (prepared by the same procedure as Example 1 except that 0.5 g of dextrin was used in place of 0.5 g of dinotefuran) was spread on another outer surface of another shelter of the triangular tube shape and put into the plastic container. The shelter treated with the gelled poison bait was removed from the plastic container 6 hours later.

The mortality (%) was observed 6 hours, one day, two days and three days, respectively, after putting the shelter treated with the gelled poison bait into the plastic container. The results of two repetitions are given below.

TABLE 2

|  | Mortality (%) | | | |
| --- | --- | --- | --- | --- |
|  | 6 hours later | 1 day later | 2 days later | 3 days later |
| Example 1 | 80 | 98 | 100 | 100 |

Example 7

The same test was performed as Example 6 except that the shelter of the triangular tube shape was left for three weeks after treated with the gelled poison bait obtained in Example 1 and then put into the plastic container.

Further, a comparative test was performed by using a gelled poison bait, which was obtained by the same procedure as Example 1 except that 5 g of water were used in place of 5 g of polyvinyl alcohol solution.

The results are given below.

TABLE 3

|  | Mortality (%) | | | |
| --- | --- | --- | --- | --- |
|  | 6 hours later | 1 day later | 2 days later | 3 days later |
| Example 1 | 80 | 93 | 95 | 100 |
| Compartative bait* | 22 | 52 | 62 | 68 |

*without polyvinyl alcohol

The above-results show that the addition of polyvinyl alcohol is effective for controlling cockroaches even after 3 weeks.

What is claimed is:

1. A gelled poison bait which comprises 0.01 to 2% by weight of 1-methyl-2-nitro-3-((tetrahydrofuryl) methyl) guanidine as an insecticidally active ingredient, 1 to 10% by weight of carrageenan, 0.1 to 3% by weight of polyvinyl alcohol, 0.85 to 28.5% by weight of fat and/or fatty oil, 3 to 80% by weight of powdered crop, starch, dextrin and/or sugar, 1 to 10% by weight of glycerin and 0.1-10% of water.

2. A method for controlling insect which comprises applying an effective amount of the gelled poison bait described in claim 1 to a location that said insect inhabits or is otherwise present.

3. The method according to claim 1, wherein the insect is a cockroach.

* * * * *